(12) United States Patent
Higashi et al.

(10) Patent No.: US 11,261,148 B2
(45) Date of Patent: Mar. 1, 2022

(54) METHOD FOR PRODUCING CARBONYL COMPOUND

(71) Applicant: DAIKIN INDUSTRIES, LTD., Osaka (JP)

(72) Inventors: Masahiro Higashi, Osaka (JP); Satoru Yoneda, Osaka (JP); Sumi Ishihara, Osaka (JP); Yosuke Kishikawa, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 16/978,997

(22) PCT Filed: Mar. 7, 2019

(86) PCT No.: PCT/JP2019/009024
§ 371 (c)(1),
(2) Date: Sep. 8, 2020

(87) PCT Pub. No.: WO2019/172360
PCT Pub. Date: Sep. 12, 2019

(65) Prior Publication Data
US 2021/0002199 A1 Jan. 7, 2021

(30) Foreign Application Priority Data
Mar. 9, 2018 (JP) .............................. JP2018-043572

(51) Int. Cl.
| C07C 45/34 | (2006.01) |
| B01J 23/44 | (2006.01) |
| C07B 41/06 | (2006.01) |
| C07C 51/373 | (2006.01) |

(52) U.S. Cl.
CPC ............. *C07C 45/34* (2013.01); *B01J 23/44* (2013.01); *C07B 41/06* (2013.01); *C07C 51/373* (2013.01)

(58) Field of Classification Search
CPC .................................................. C07C 45/34
See application file for complete search history.

(56) References Cited

U.S. PATENT DOCUMENTS

| 5,136,105 A | 8/1992 | Wenzel |
| 8,507,728 B2 * | 8/2013 | Kaneda .............. C07C 45/34 568/360 |
| 2011/0288340 A1 | 11/2011 | Kaneda et al. |
| 2012/0197036 A1 | 8/2012 | Kaneda et al. |

FOREIGN PATENT DOCUMENTS

| EP | 0 519 084 | 12/1992 |
| JP | 5-85973 | 4/1993 |
| JP | 5-294885 | 11/1993 |
| JP | 2003-73324 | 3/2003 |
| JP | 2011-88861 | 5/2011 |
| JP | 5524861 | 6/2014 |
| JP | 5613150 | 10/2014 |
| WO | 2010/061807 | 6/2010 |
| WO | 2011/043459 | 4/2011 |

OTHER PUBLICATIONS

Tang et al., "Polymer-Supported Pd(II) Wacker-Type Catalysts II. Application in the Oxidation of Dec-1-ene", Journal of Catalysis, 1993, vol. 142, pp. 540-551.
Yokota et al., "Selective Wacker-type oxidation of terminal alkenes and dienes using the Pd(II)/molybdovanadophosphate (NPMoV)/$O_2$ system", Tetrahedron Letters, 2002, vol. 43, pp. 8887-8891.
Cornell et al., "Discovery of and Mechamstic Insight into a Ligand-Modulated Palladium-Catalyzed Wacker Oxidation of Styrenes Using TBHP", Journal of the American Chemical Society, 2005, vol. 127, pp. 2796-2797.
International Search Report dated May 28, 2019 in International (PCT) Application No. PCT/JP2019/009024.
Roshchin et al., "Synthesis of benzofurans via $Pd^{2+}$—catalyzed oxidative cyclization of 2-allylphenols", Journal of Organometallic Chemistry, 1998, vol. 560, pp. 163-167.
Pugin et al., "Palladium-Catalyzed Oxidation of Amino Alkenes to Cyclic Imines or Enamines and Amino Ketones", Journal of the American Chemical Society, 1983, vol. 105, pp. 6877-6881.

(Continued)

*Primary Examiner* — Sikarl A Witherspoon
(74) *Attorney, Agent, or Firm* — Wenderoth, Lind & Ponack, L.L.P.

(57) ABSTRACT

A method for producing a carbonyl compound represented by formula (1):

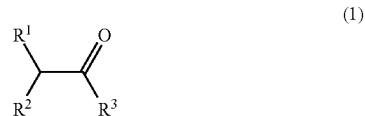

(1)

wherein $R^1$ is hydrogen or an organic group; $R^2$ is hydrogen or an organic group; and $R^3$ is hydrogen or an organic group; or two or three of $R^1$, $R^2$, and $R^3$ may be linked to form a ring that may have at least one substituent, the method comprising step A of oxidizing an olefin compound represented by formula (2):

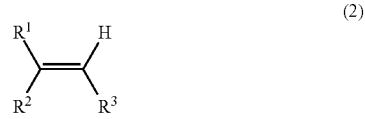

(2)

wherein symbols are as defined above, by an oxidizing agent in the presence of (a) a non-alcohol organic solvent, (b) water, (c) a metal catalyst, and (d) an additive represented by the formula: MXn, wherein M is an element belonging to any one of Group 1, Group 2, Group 13, Group 14, and Group 15 in the periodic table, or $NR_4$, wherein R is hydrogen or a $C_{1-10}$ organic group; X is halogen; and n is a number of 1 to 5.

17 Claims, No Drawings

(56) References Cited

OTHER PUBLICATIONS

Li et al., "A Novel and Efficient Total Synthesis of Cephalotaxine", Canadian Journal of Chemistry, 1984, vol. 62, 1392, pp. 1-10.
Timothy T. Wenzel, "Oxidation of Olefins to Aldehydes Using a Palladium-Copper Catalyst", J. Chem. Soc., Chem. Commun., 1993, pp. 862-864.
Kulkarni et al., "Greening the Wacker process", Tetrahedron Letters, 2013, vol. 54, pp. 2293-2295.
Extended European Search Report dated Nov. 3, 2021 in corresponding European Patent Application No. 19764300.
Michel et al., "The Wacker Oxidation", Chapter 2, Organic Reactions, vol. 84, Apr. 22, 2014.

* cited by examiner

METHOD FOR PRODUCING CARBONYL COMPOUND

TECHNICAL FIELD

The present disclosure relates to a method for producing a carbonyl compound.

BACKGROUND ART

As carbonyl compound production methods, those described in Patent Literature 1 to 3 and Non-patent Literature 1 to 3 are known.

CITATION LIST

Patent Literature

PTL 1: Japanese Patent No. 5613150
PTL 2: Japanese Patent No. 5524861
PTL 3: Japanese Unexamined Patent Application No. 2003-73324

Non-Patent Literature

NPL 1: Journal of Catalysis, 142, 1993, pp. 540-551
NPL 2: Tetrahedron Letters, 43, 2002, pp. 9887-8891
NPL 3: J. Am. Chem. Soc., 127, 2005, pp. 2796-2797

SUMMARY OF INVENTION

Technical Problem

However, further development of a carbonyl compound production method is desired.

Solution to Problem

The present specification provides the following solutions to the above problem.

Item 1. A method for producing a carbonyl compound represented by formula (1):

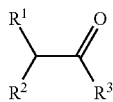

(1)

wherein
$R^1$ is hydrogen or an organic group;
$R^2$ is hydrogen or an organic group; and
$R^3$ is hydrogen or an organic group; or
two or three of $R^1$, $R^2$, and $R^3$ may be linked to form a ring that may have at least one substituent,
the method comprising step A of oxidizing an olefin compound represented by formula (2):

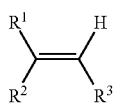

(2)

wherein the symbols are as defined above, by an oxidizing agent in the presence of (a) a non-alcohol organic solvent,
(b) water,
(c) a metal catalyst, and
(d) an additive represented by the formula: MXn
wherein
M is an element belonging to any one of Group 1, Group 2, Group 13, Group 14, and Group 15 in the periodic table, or $NR_4$, wherein
R is hydrogen or a $C_{1-10}$ organic group;
X is halogen; and
n is a number of 1 to 5.

Item 2. The production method according to Item 1, wherein $R^1$ and $R^2$ are independently hydrogen, $C_{1-10}$ alkyl optionally having at least one substituent, $C_{1-10}$ aromatic group optionally having at least one substituent, or a $C_{1-10}$ heterocyclic group optionally having at least one substituent.

Item 3. The production method according to Item 2, wherein $R^1$ and $R^2$ are independently hydrogen; $C_{1-4}$ alkyl optionally having at least one substituent, wherein the at least one substituent is independently selected from the group consisting of hydroxyl, amino, carboxyl, sulfonic acid, phosphonic acid, and salts thereof; a $C_{1-10}$ aromatic group optionally having at least one substituent; or a $C_{1-10}$ heterocyclic group optionally having at least one substituent.

Item 4. The production method according to any one of Items 1 to 3 or Item 2, wherein $R^3$ is hydrogen; $C_{1-20}$ alkyl optionally having at least one substituent; a $C_{1-20}$ aromatic group optionally having at least one substituent; or a $C_{1-20}$ heterocyclic group optionally having at least one substituent.

Item 5. The production method according to Item 4, wherein $R^3$ is hydrogen; $C_{1-20}$ alkyl optionally having at least one substituent, wherein the at least one substituent is independently selected from the group consisting of hydroxyl, amino, carboxyl, sulfonic acid, phosphonic acid, and salts thereof; a $C_{1-10}$ aromatic group optionally having at least one substituent; or a $C_{1-10}$ heterocyclic group optionally having at least one substituent.

Item 6. The production method according to any one of Items 1 to 5, wherein the non-alcohol organic solvent (a) is at least one solvent selected from the group consisting of amide solvents, ether solvents, nitrile solvents, sulfoxide solvents, aromatic solvents, ester solvents, ketone solvents, fluorine-based solvents, carbonate solvents, carboxylic acid solvents, and ionic liquid.

Item 7. The production method according to Item 6, wherein the non-alcohol organic solvent (a) is at least one solvent selected from the group consisting of amide solvents, ether solvents, aromatic solvents, nitrile solvents, and carboxylic acid solvents.

Item 8. The production method according to Item 7, wherein the non-alcohol organic solvent (a) is an amide solvent.

Item 9. The production method according to any one of Items 1 to 8, wherein the metal catalyst (c) is a transition metal catalyst.

Item 10. The production method according to Item 9, wherein the metal catalyst (c) is at least one catalyst selected from the group consisting of Ti catalysts, Cr catalysts, Fe catalysts, Co catalysts, Ni catalysts, Mo catalysts, Ru catalysts, Rh catalysts, Pd catalysts, W catalysts, Ir catalysts, Pt catalysts, and Au catalysts.

Item 11. The production method according to Item 10, wherein the metal catalyst (c) is at least one catalyst selected from the group consisting of Fe catalysts, Ru catalysts, Pd catalysts, and W catalysts.

Item 12. The production method according to Item 11, wherein the metal catalyst (c) is a Pd catalyst.

Item 13. The production method according to any one of Items 1 to 12, wherein the additive (d) is an additive represented by the formula: MXn
wherein M is an element belonging to any one of Group 1, Group 2, Group 13, Group 14, and Group 15 in the periodic table, or $NR_4$,
wherein
R is hydrogen or a $C_{1-10}$ organic group;
X is halogen; and
n is a number of 1 to 3.
Item 14. The production method according to Item 13, wherein the additive (d) is an additive represented by the formula: MXn
wherein
M is Li, Na, B, Mg, Al, Si, P, K, Ca, Cs, or $NH_4$;
X is fluorine, chlorine, bromine, or iodine; and
n is a number of 1 to 3.
Item 15. The production method according to Item 14, wherein the additive (d) is an additive represented by the formula: MXn
wherein
M is Li, Na, K, or $NH_4$;
X is chlorine; and
n is a number of 1.
Item 16. The production method according to any one of Items 1 to 15, wherein the oxidizing agent is at least one member selected from the group consisting of molecular oxygen, ozone, quinones, hypervalent iodine compounds, and peroxyacids.
Item 17. The production method according to Item 16, wherein the oxidizing agent is molecular oxygen.

Advantageous Effects of Invention

According to the present disclosure, a novel carbonyl compound production method is provided.

DESCRIPTION OF EMBODIMENTS

1. Terms

The symbols and the abbreviations in this specification are to be interpreted as having the general meanings in the related technical field to which the present invention pertains, according to the context of this specification, unless otherwise specified.

In this specification, the term "comprise" or "contain" is intended to encompass the meanings of "consist essentially of" and "consist of."

The steps, treatments, or operations in this specification can be performed at room temperature, unless otherwise specified.

In this specification, room temperature refers to a temperature in the range of 10 to 40° C.

In this specification, the term "Cn-m" (herein, n and m are numbers) indicates that the carbon number is n or more and m or less, as would usually be understood by a person skilled in the art.

In this specification, the term "organic compound" is understood in the ordinary sense, and can be a compound having at least one carbon and at least one hydrogen.

In this specification, the fluorinated organic compound means a compound that can be generated by fluorinating an organic compound, and may not contain hydrogen.

In this specification, unless otherwise specified, examples of "halo (group)" may include fluoro (group), chloro (group), bromo (group), and iodo (group).

In this specification, unless otherwise specified, examples of "halogen (atom)" include fluorine (atom), chlorine (atom), bromine (atom), and iodine (atom).

In this specification, the term "organic group" refers to a group containing at least one carbon (or a group formed by removing one hydrogen from an organic compound).

In this specification, the "organic group" can be a non-aromatic organic group (or aliphatic organic group), or an aromatic organic group.

Examples of "organic group" include the following:
alkyl optionally having at least one substituent,
alkenyl optionally having at least one substituent,
alkynyl optionally having at least one substituent,
cycloalkyl optionally having at least one substituent,
cycloalkenyl optionally having at least one substituent,
cycloalkadienyl optionally having at least one substituent,
aryl optionally having at least one substituent,
aralkyl optionally having at least one substituent,
a non-aromatic heterocyclic group optionally having at least one substituent,
heteroaryl optionally having at least one substituent,
cyano,
aldehyde,
$R^rO—$,
$R^rCO—$,
$R^rSO_2—$,
$R^rOCO—$, and
$R^rOSO_2—$
wherein $R^r$ is independently
alkyl optionally having at least one substituent,
alkenyl optionally having at least one substituent,
alkynyl optionally having at least one substituent,
cycloalkyl optionally having at least one substituent,
cycloalkenyl optionally having at least one substituent,
cycloalkadienyl optionally having at least one substituent,
aryl optionally having at least one substituent,
aralkyl optionally having at least one substituent,
a non-aromatic heterocyclic group optionally having at least one substituent, or
hetezoaryl optionally having at least one substituent.

In this specification, the "organic group" can be, for example, a hydrocarbon optionally having at least one substituent (the hydrocarbon into which at least one moiety selected from the group consisting of $—NR^o—$, $=N—$, $—N=$, $—O—$, $—S—$, $—C(=O)O—$, $—OC(=O)—$, $—C(=O)—$, $—S(=O)—$, $—S(=O)_2—$, $—S(=O)_2—NR^o—$, $—NR^o—S(=O)_2—$, $—S(=O)—NR^o—$, and $—NR^o—S(=O)—$ wherein $R^o$ is independently hydrogen or an organic group may be inserted).

In this specification, the "hydrocarbon" can be non-aromatic hydrocarbon (or aliphatic hydrocarbon), or aromatic hydrocarbon.

As can be generally understood based on common knowledge in the chemical field, examples of the hydrocarbon into which a hetero atom is inserted may include a non-aromatic heterocyclic group and heteroaryl.

In this specification, the number of carbon atoms of the "hydrocarbon" in the "hydrocarbon optionally having at least one substituent" is, for example, 1 to 100, 1 to 80, 1 to 60, 1 to 40, 1 to 30, 1 to 20, or 1 to 10 (e.g., 1, 2, 3, 4, 5, 6, 7, 8, 9, or 10).

In this specification, examples of substituents in hydrocarbon optionally having at least one substituent, alkyl optionally having at least one substituent, alkenyl optionally having at least one substituent, alkynyl optionally having at least one substituent, cycloalkyl optionally having at least one substituent, cycloalkenyl optionally having at least one substituent, cycloalkadienyl optionally having at least one substituent, aryl optionally having at least one substituent, and aralkyl optionally having at least one substituent include halo, nitro, cyano, oxo, thioxo, sulfo, sulfamoyl, sulfinamoyl, and sulfenamoyl.

The number of substituents is within the range of one to the maximum replaceable number (e.g., one, two, three, four, five, or six).

In this specification, examples of "hydrocarbon" include alkyl, alkenyl, alkynyl, cycloalkyl, cycloalkenyl, cycloalkadienyl, aryl, aralkyl, and combinations thereof.

In this specification, unless otherwise specified, examples of "alkyl" include linear or branched $C_{1-10}$ alkyl, such as methyl, ethyl, propyl, isopropyl, n-butyl, isobutyl, sec-butyl, tert-butyl, pentyl, isopentyl, neopentyl, hexyl, heptyl, octyl, nonyl, and decyl.

Examples of "alkyl optionally having at least one substituent" include haloalkyl and fluoroalkyl.

In this specification, "haloalkyl" is alkyl having at least one hydrogen replaced with a halo group.

In this specification, "fluoroalkyl" is alkyl having at least one hydrogen replaced with fluorine.

In this specification, the number of fluorine atoms contained in the "fluoroalkyl" is one or more (e.g., 1 to 3, 1 to 6, 1 to 12, and 1 to the maximum replaceable number).

As a person skilled in the art would normally understand, the suffix "perhalogeno" means that all hydrogen atoms are replaced with a halo group.

As a person skilled in the art would normally understand, the suffix "perfluoro" means that all hydrogen atoms are replaced with a halo group.

"Fluoroalkyl" includes perfluoroalkyl.

Perfluoroalkyl refers to alkyl having all hydrogen atoms replaced with fluorine. Examples of perfluoroalkyl include trifluoromethyl ($CF_3$—) and pentafluoroethyl ($C_2F_5$—).

In this specification, "fluoroalkyl" means, for example, fluoroalkyl having 1 to 20 carbon atoms, 1 to 12 carbon atoms, 1 to 6 carbon atoms, 1 to 4 carbon atoms, 1 to 3 carbon atoms, 6 carbon atoms, 5 carbon atoms, 4 carbon atoms, 3 carbon atoms, 2 carbon atoms, or 1 carbon atom.

In this specification, "fluoroalkyl" can be linear or branched fluoroalkyl.

In this specification, examples of "fluoroalkyl" include fluoromethyl, difluoromethyl, trifluoromethyl ($CF_3$—), 2,2,2-trifluoroethyl, pentafluoroethyl ($C_2F_5$—), tetrafluoropropyl (e.g., $HCF_2CF_2CH_2$—), hexafluoropropyl (e.g., $(CF_3)_2CH$—), nonafluorobutyl, octafluoropentyl (e.g., $HCF_2CF_2CF_2CF_2CH_2$—), and tridecafluorohexyl.

In this specification, unless otherwise specified, examples of "alkenyl" include linear or branched $C_{2-10}$ alkenyl, such as vinyl, 1-propen-1-yl, 2-propen-1-yl, isopropenyl, 2-buten-1-yl, 4-penten-1-yl, and 5-hexen-1-yl.

In this specification, unless otherwise specified, examples of "alkynyl" include linear or branched $C_{2-10}$ alkynyl, such as ethynyl, 1-propyn-1-yl, 2-propyn-1-yl, 4-pentyn-1-yl, and 5-hexyne-1-yl.

In this specification, unless otherwise specified, examples of "cycloalkyl" include $C_{3-7}$ cycloalkyl, such as cyclopropyl, cyclobutyl, cyclopentyl, cyclohexyl, and cycloheptyl.

In this specification, unless otherwise specified, examples of "cycloalkenyl" include $C_{3-7}$ cycloalkenyl, such as cyclopropenyl, cyclobutenyl, cyclopentenyl, cyclohexenyl, and cycloheptenyl.

In this specification, unless otherwise specified, examples of "cycloalkadienyl" include $C_{4-10}$ cycloalkadienyl, such as cyclobutadienyl, cyclopentadienyl, cyclohexadienyl, cycloheptadienyl, cyclooctadienyl, cyclononadienyl, and cyclodecadienyl.

In this specification, unless otherwise specified, the term "aryl" may be monocyclic, bicyclic, tricyclic, or tetracyclic.

In this specification, unless otherwise specified, the term "aryl" may be $C_{6-18}$ aryl.

In this specification, unless otherwise specified, examples of "aryl" include phenyl, 1-naphthyl, 2-naphthyl, 2-biphenyl, 3-biphenyl, 4-biphenyl, and 2-anthryl.

In this specification, unless otherwise specified, examples of "aralkyl" include benzyl, phenethyl, diphenylmethyl, 1-naphthyl methyl, 2-naphthyl methyl, 2,2-diphenylethyl, 3-phenylpropyl, 4-phenylbutyl, 5-phenylpentyl, 2-biphenylylmethyl, 3-biphenylylmethyl, and 4-biphenylylmethyl.

In this specification, unless otherwise specified, the term "non-aromatic heterocyclic group" may be monocyclic, bicyclic, tricyclic, or tetracyclic.

In this specification, unless otherwise specified, the term "non-aromatic heterocyclic group" may be, for example, a non-aromatic heterocyclic group containing, in addition to carbon, 1 to 4 heteroatoms selected from oxygen, sulfur, and nitrogen as a ring-constituting atom.

In this specification, unless otherwise specified, the term "non-aromatic heterocyclic group" may be saturated or unsaturated.

In this specification, unless otherwise specified, examples of "non-aromatic heterocyclic group" include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), azetidinyl (e.g., 1-azetidinyl and 2-azetidinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, and the like.

In this specification, unless otherwise specified, examples of "heteroaryl" include monocyclic aromatic heterocyclic groups (e.g., 5- or 6-membered monocyclic aromatic heterocyclic groups), and aromatic fused heterocyclic groups (e.g., 5- to 18-membered aromatic fused heterocyclic groups).

In this specification, unless otherwise specified, examples of "5- or 6-membered monocyclic aromatic heterocyclic groups" include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazoyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), pyrazinyl, and the like.

In this specification, unless otherwise specified, examples of "5- to 18-membered aromatic fused heterocyclic groups" include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo(c)furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl), and the like.

Unless otherwise specified, in this specification, examples of substituents in each of the "non-aromatic heterocyclic groups optionally having at least one substituent," and "heteroaryl optionally having at least one substituent" include hydrocarbon having at least one substituent, halo, nitro, cyano, oxo, thioxo, sulfo, sulfamoyl, sulfinamoyl, and sulfenamoyl.

The number of substituents can be within the range of 1 to the maximum replaceable number (e.g., 1, 2, 3, 4, 5, or 6).

2. Production Method

In this specification, the carbonyl compound production method is a method for producing a carbonyl compound (in this specification, referred to as carbonyl compound (1)) represented by formula (1):

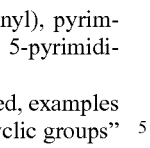

wherein
$R^1$ is hydrogen or an organic group;
$R^2$ is hydrogen or an organic group; and
$R^3$ is hydrogen or an organic group; or
two or three of $R^1$, $R^2$, and $R^3$ may be linked to form a ring optionally having at least one substituent,
the method comprising step A of oxidizing an olefin compound (in this specification, referred to as olefin compound (2)) represented by formula (2):

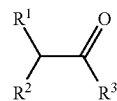

wherein symbols are as defined above, by an oxidizing agent in the presence of
(a) a non-alcohol organic solvent,
(b) water,
(c) a metal catalyst, and
(d) an additive represented by the formula: MXn,
wherein
M is an element belonging to any one of Group 1, Group 2, Group 13, Group 14, and Group 15 in the periodic table, or $NR_4$, wherein R is hydrogen or a $C_{1-10}$ organic group;
X is halogen; and
n is a number of 1 to 5, preferably 1 to 3, and more preferably 1 or 2.

The reaction of step A may be carried out by mixing the above by a known method.

These can be added to the reaction system in any order.
These may be added to the reaction system all at once, separately in some parts, or sequentially.

2.1. Substrate Compound and Target Compound

The carbonyl compound (1), which is the target product of step A, can be produced by the reaction of step A using an olefin compound (2) that is a substrate.

The symbols in formulae (1) and (2) are as defined above.
It is preferable that $R^1$ and $R^2$ are independently hydrogen or a $C_{1-30}$ organic group. More preferably, $R^1$ and $R^2$ are hydrogen or $C_{1-30}$ alkyl optionally having at least one substituent (preferably $C_{1-20}$ alkyl), $C_{1-20}$ aromatic group, or a $C_{1-20}$ heterocyclic group (preferably 3- to 21-membered heterocyclic group having 1 to 20 carbon atoms); and even more preferably hydrogen, $C_{1-10}$ alkyl optionally having at least one substituent, at least one $C_{1-10}$ aromatic group, or at least one $C_{1-10}$ heterocyclic group.

Still more preferably, $R^1$ and $R^2$ are hydrogen, $C_{1-4}$ alkyl (the $C_{1-4}$ alkyl optionally having at least one substituent, wherein the at least one substituent is independently selected from the group consisting of hydroxyl, amino, carboxyl, sulfonic acid, phosphonic acid, and salts thereof); $C_{1-10}$ aromatic group; or $C_{1-10}$ heterocyclic group (preferably, 3- to 11-membered heterocyclic group having 1 to 10 carbon atoms. Even more preferably, $R^1$ and $R^2$ are hydrogen or $C_{1-4}$ alkyl optionally having a substituent; and particularly preferably $R^1$ and $R^2$ are hydrogen.

Of these, $R^1$ is preferably $C_{1-30}$ linear alkyl that may be replaced with at least one hydroxyl, more preferably $C_{1-20}$ linear alkyl that may be replaced with at least one hydroxyl, and even more preferably $C_{1-10}$ linear alkyl that may be substituted with at least one hydroxyl.

$R^3$ is preferably hydrogen or a $C_{1-30}$ organic group; more preferably hydrogen, $C_{1-20}$ alkyl optionally having a substituent, a $C_{1-20}$ aromatic group, or a $C_{1-20}$ heterocyclic group having 1 to 20 carbon atoms (preferably a 3- to 21-membered heterocyclic group having 1 to 20 carbon atoms). Even more preferably, $R^3$ is hydrogen; $C_{1-20}$ alkyl ($C_{1-20}$ alkyl optionally having at least one substituent, wherein the at least one substituent is selected from the group consisting of hydroxyl, amino, carboxyl, sulfonic acid, phosphonic acid, and salts thereof); a $C_{1-10}$ aromatic group; or a $C_{1-10}$ heterocyclic group (preferably 3- to 11-membered heterocyclic group having 1 to 10 carbon atoms).

Even more preferably, $R^3$ is $C_{1-20}$ alkyl optionally having at least one substituent, wherein the at least one substituent is preferably selected from the group consisting of hydroxyl, amino, carboxyl, sulfonic acid, phosphonic acid, and salts thereof; and particularly preferably $C_{1-10}$ alkyl optionally having a substituent; and even more preferably hydrogen, $C_{1-4}$ alkyl optionally having at least one substituent, wherein the at least one substituent is independently selected from the group consisting of hydroxyl, amino, carboxyl, sulfonic acid, phosphonic acid, and salts thereof; a $C_{1-10}$ aromatic group; or $C_{1-10}$ heterocyclic group.

Examples of substituents of the "ring optionally having at least one substituent" formed by linking two or three of $R^1$, $R^2$, and $R^3$ include organic groups.

The "ring" in the "ring optionally having at least one substituent" is preferably a 3- to 40-membered ring, and more preferably a 3- to 14-membered ring; and is preferably monocyclic or polycyclic (e.g., bicyclic or tricyclic) ring. The polycyclic ring includes a bridged ring.

Preferable examples of the ring include a benzene ring, a naphthalene ring, an anthracene ring, a cyclohexane ring, a cyclopentane ring, a furan ring, and a crown ether ring.

2.2. Organic Solvent (a)

Examples of the organic solvent (a) include amide solvents, ether solvents, nitrile solvents, sulfoxide solvents, aromatic solvents, ionic liquid solvents, non-aromatic solvents, ketone solvents, ester solvents, carbonate solvents, fluorine-based solvents, halogenated hydrocarbon solvents, and carboxylic acid solvents.

Preferable examples of the amide solvent include solvents consisting essentially of an amide represented by the formula: $R^{N1}R^{N2}$—N—$CR^C$=O, wherein $R^{N1}$ is $C_{1-10}$ alkyl (preferably $C_{1-6}$ alkyl, more preferably $C_{1-3}$ alkyl, and even more preferably $C_{1-2}$ alkyl (methyl or ethyl)), $R^{N2}$ is $C_{1-10}$ alkyl (preferably $C_{1-2}$ alkyl, more preferably $C_{1-3}$ alkyl, and even more preferably $C_{1-2}$ alkyl (methyl or ethyl), and $R^C$ is hydrogen, or $C_{1-3}$ chain hydrocarbon (preferably methyl, ethyl, or ethenyl); or $R^{N2}$ and $R^C$ may be linked to form a $C_{2-4}$ ancandiyl chain (preferably propane-1,3-diyl)).

Examples of the amide solvent include N,N-dimethylformamide, N,N-dimethylacetamide, N-methylpyrrolidone, 1,3-dimethyl-2-imidazolidinone, N,N-dimethylacrylamide, N,N-dimethylacetoacetamide, N,N-diethylformamide, and N,N-diethylacetamide.

Preferable examples include N,N-dimethylformamide, N-methylpyrrolidone, and N,N-dimethylacetoacetamide.

More preferable examples include N,N-dimethylacetoacetamide.

Examples of the ether solvent include diethyl ether, tetrahydrofuran, diisopropyl ether, methyl-t-butyl ether, dioxane, dimethoxyethane, diglyme, anisole, phenetole, 1,1-dimethoxycyclohexane, diisoamyl ether, and cyclopentyl methyl ether.

Preferable examples include tetrahydrofuran, methyl-t-butyl ether, and cyclopentyl methyl ether.

Examples of the nitrile solvent include acetonitrile and benzonitrile.

Preferable examples include acetonitrile.

Examples of the sulfoxide solvent include dimethyl sulfoxide and sulfolane.

Preferable examples include dimethyl sulfoxide.

Specific examples of the aromatic solvent include benzene, toluene, xylene, tetralin, veratrol, ethylbenzene, diethylbenzene, methylnaphthalene, nitrobenzene, o-nitrotoluene, mesitylene, indene, diphenyl sulfide, and anisole.

Examples of the ionic liquid solvent include 1-allyl-3-methylimidazolium chloride ([Amim][Cl]), 1-ethyl-3-methylimidazolium acetate ([$C_2$mim][Ac]), 1-ethyl-3-methylimidazolium diethylphosphate ([$C_2$mim][DEP]), 1-ethyl-3-methylimidazolium methylphosphonate ([$C_2$mim][MEP], 1-butyl-3-methylimidazolium acetate ([$C_4$mim][Ac]), 1-ethyl-3-methylimidazolium phosphinate ((([$C_2$mim][HPO]), 1-ethyl-3-methylimidazolium chloride ([EMIM][Cl]), 1-butyl-3-methylimidazolium chloride ([BMIM][Cl]), 1-ethyl-3-methylimidazolium bromide ([EMIM][Br]), 1-methyl-3-hexyl imidazolium tetrafluoroborate ([EMIM][BF4]), 1-butyl-3-methylimidazolium tetrafluoroborate ([BMIM][BF4]), 1-ethyl-3-methylimidazolium hexafluorophosphate ([EMIM][PF6]), and 1-butyl-3-methylimidazolium hexafluorophosphate([BMIM][PF6]).

Preferable examples include 1-butyl-3-methylimidazolium tetrafluoroborate ([BMIM][BF4]).

Examples of non-aromatic solvents include pentane, hexane, heptane, octane, cyclohexane, decahydronaphthalene, n-decane, isododecane, and tridecane.

Examples of ketone solvents include acetone, methyl ethyl ketone, diethyl ketone, hexanone, methyl isobutyl ketone, heptanone, diisobutyl ketone, acetonyl acetate, methyl hexanone, acetophenone, cyclohexanone, diacetone alcohol, propiophenone, and isophorone.

Examples of ester solvents include ethyl acetate, isopropyl acetate, butyl acetate, diethyl malonate, 3-methoxy-3-methylbutyl acetate, γ-butyrolactone, ethylene carbonate, propylene carbonate, dimethyl carbonate, α-acetyl-γ-butyrolactone, amyl acetate, ethylene glycol monomethyl ether acetate, and propylene glycol monomethyl ether acetate (PGMEA).

Examples of fluorine-based solvents include perfluorobenzene, trifluorotoluene, ditrifluorobenzene, and trifluoroethanol.

Examples of carbonate solvents include tetralin dimethyl carbonate, methyl ethyl carbonate, diethyl carbonate, ethylene carbonate, and propylene carbonate.

Examples of halogenated hydrocarbon solvents include dichloromethane, dichloroethane, chloroform, carbon tetrachloride, tetrachloroethane, trichloroethane, chlorobenzene, dichlorobenzene, and chlorotoluene.

Examples of carboxylic acid solvents include acetic acid and propionic acid.

The non-alcohol organic solvent (a) is preferably at least one solvent selected from the group consisting of amide solvents, ether solvents, nitrile solvents, sulfoxide solvents, aromatic solvents, ester solvents, carboxylic acid solvents, and ionic liquid solvents.

The non-alcohol organic solvent (a) is more preferably at least one solvent selected from the group consisting of amide solvents, ether solvents, aromatic solvents, nitrile solvents, and carboxylic acid solvents.

The non-alcohol organic solvent (a) is even more preferably an amide solvent.

The non-alcohol organic solvent (a) may be used alone, or in a combination of two or more. In such a combination, it is also preferable to combine the preferable solvent (more preferable solvent, and even more preferable solvent) Mentioned above with another solvent.

The non-alcohol organic solvent (a) is more preferably at least one solvent selected from the group consisting of amide solvents, ether solvents, aromatic solvents, nitrile solvents, and carboxylic acid solvents.

The amount of the non-alcohol organic solvent (a) used can be suitably determined in view of technical knowledge. For example, the amount of the non-alcohol organic solvent (a) is an amount exceeding the amount capable of completely dissolving the olefin compound (2).

The non-alcohol organic solvent (a) is more preferably an amide solvent.

2.3. Water (b)

The source of the water is not limited, as long as it does not significantly impair the production of the target product. Examples include tap water, deionized water, and pure water.

The lower limit of the amount of water is preferably 0.1 moles, more preferably 0.5 moles, and even more preferably 0.8 moles, relative to 1 mole of the olefin compound (2).

The upper limit of the amount of water is preferably 100 moles, more preferably 50 moles, and even more preferably 30 moles, relative to 1 mole of the olefin compound (2).

The amount of the water is preferably within the range of 0.1 to 100 moles, more preferably within the range of 0.5 to 50 moles, and even more preferably 0.8 to 30 moles, relative to 1 mole of the olefin compound (2).

By carrying out the reaction with such an amount, the target product can be efficiently obtained.

2.4. Metal Catalyst (c)

The metal catalyst (c) is preferably a transition metal catalyst.

The metal catalyst (c) is more preferably at least one catalyst selected from the group consisting of Ti catalysts, Cr catalysts, Fe catalysts, Co catalysts, Ni catalysts, Mo catalysts, Ru catalysts, Rh catalysts, Pd catalysts, W catalysts, Ir catalysts, Pt catalysts, and Au catalysts.

The metal catalyst (c) is even more preferably at least one catalyst selected from the group consisting of Fe catalysts, Ru catalysts, Pd catalysts, and W catalysts.

The metal catalyst (c) is even more preferably a Pd catalyst.

The lower limit of the amount of the metal catalyst (c) is preferably 0.00001 moles, more preferably 0.00005 moles, and even more preferably 0.0001 moles, relative to 1 mole of the olefin compound (2).

The upper limit of the amount of the metal catalyst (c) is preferably 10 moles, more preferably 5.0 moles, and even more preferably 1.2 moles, relative to 1 mole of the olefin compound (2).

The amount of the metal catalyst (c) is preferably within the range of 0.00001 to 10 moles, more preferably within the range of 0.00005 to 5.0 moles, and even more preferably within the range of 0.0001 to 1.2 moles, relative to 1 mole of the olefin compound (2).

By carrying out the reaction with such an amount, the target product can be efficiently obtained.

Additive (d)

In the additive represented by the formula: $MX_n$, M is an element belonging to any one of Group 1, Group 2, Group 13, Group 14, and Group 15 in the periodic table, or $NR_4$, wherein R is hydrogen or a $C_{1-10}$ organic group. M is preferably Li, Na, B, Mg, Al, Si, P, K, Ca, Cs, or $NH_4$; more preferably Li, Na, K, or NH4; and even more preferably Na or K.

In the additive represented by the formula: $MX_n$, X is halogen, preferably fluorine, chlorine, bromine, or iodine, and more preferably chlorine.

The additive (d) is preferably an additive represented by the formula: $MX_n$, wherein M is an element belonging to any one of Group 1, Group 2, Group 13, Group 14, and Group 15 in the periodic table, or $NR_4$, wherein R is hydrogen or a $C_{1-10}$ organic group; X is halogen; and n is a number of 1 to 3.

The additive (d) is more preferably an additive represented by the formula: $MX_n$, wherein M is Li, Na, B, Mg, Al, Si, P, K, Ca, Cs, or $NH_4$; X is fluorine, chlorine, bromine, or iodine; and n is a number of 1 to 3.

The additive (d) is even more preferably an additive (e.g., NaCl, KCl) represented by the formula: $MX_n$, wherein M is Li, Na, K, or $NH_4$; X is chlorine; and n is a number of 1.

The lower limit of the amount of the additive (d) used is preferably 0.001 moles, more preferably 0.005 moles, and even more preferably 0.01 moles, relative to 1 mole of the olefin compound (2).

The upper limit of the amount of the additive (d) is preferably 10 moles, more preferably 5.0 moles, and even more preferably 1.2 moles, relative to 1 mole of the olefin compound (2). The amount of the additive (d) used is, relative to 1 mole of the olefin compound (2), preferably within the range of 0.001 to 10 moles, more preferably within the range of 0.005 to 5.0 moles, and even more preferably within the range of 0.01 to 1.2 moles.

By carrying out the reaction with such an amount, the target product can be efficiently obtained.

Oxidizing Agent

The oxidizing agent is preferably at least one member selected from the group consisting of molecular oxygen, ozone, quinone, hypervalent iodine compound, and peroxyacid represented by the formula of organic peroxyacid: R—O—O—H, wherein R is —$SO_3H$, —$C(=O)_3$, or —$COR^a$, and $R^a$ is hydrocarbon optionally having at least one substituent), inorganic peroxyacid, and salts thereof and mixtures thereof.

The oxidizing agent is more preferably at least one member selected from the group consisting of molecular oxygen, quinone, and peroxyacid.

Examples of the quinone include 1,4-benzoquinone that may have at least one substituent, or that may be condensed with one or two benzene rings optionally having at least one substituent, and 1,2-benzoquinone optionally having at least one substituent.

Preferable examples of the quinone include 1,4-benzoquinone optionally having at least one substituent.

Examples of the substituent include alkyl, alkenyl, aryl, aralkyl, alkoxy, hydroxy-containing group, carboxy-containing group, thiol-containing group, amino-containing group, and halogen atom.

Examples of the "quinone" include p-benzoquinone, 2,5-dihydroxy-p-benzoquinone, 2-hydroxy-p-benzoquinone, tetrahydroxy-p-benzoquinone, 1,4-naphthoquinone, 2-hydroxy-1,4-naphthoquinone, 2-methyl-p-benzoquinone, 2-methyl-1,4-naphthoquinone, 2,5-dimethoxy-1,4-benzoquinone, 2,5-di-tert-butyl-1,4-naphthoquinone, and alizarin.

Examples of the "hypervalent iodine compound" include 2-iodoxybenzoic acid (IBX), Dess-Martin periodinane (DMP), and (diacetoxylodo)benzene.

Examples of the above "organic peroxyacid" include tert-butyl hydroperoxide (TBHP), metachloroperbenzoic acid, peracetic acid, perbenzoic acid, and cumene hydroperoxide.

Examples of the "inorganic peroxyacid, and salts thereof and mixtures thereof" include hydrogen peroxide, potassium persulfate, a mixture of potassium hydrogen persulfate-potassium hydrogen sulfate-potassium sulfate, hypoperchloric acid, permanganic acid, and dichromic acid.

Preferable examples of the oxidizing agent include tert-butyl hydroperoxide (TBHP) 2-iodoxybenzoic acid (IBX), Dess-Martin periodinane (DMP), (diacetoxyiodo)benzene, metachloroperbenzoic acid, hydrogen peroxide, peracetic acid, perbenzoic acid, cumene hydroperoxide, potassium persulfate, a mixture of potassium hydrogen persulfate-potassium hydrogen sulfate-potassium sulfate, hypoperchloric acid, permanganic acid, and dichromic acid.

The above oxidizing agents can be used alone, or in a combination of two or more.

The oxidizing agent is more preferably molecular oxygen.

When molecular oxygen is used as the oxidizing agent, the reaction system may be placed in an oxygen atmosphere. Alternatively, a gas containing molecular oxygen may pass through the reaction system, or may be placed in an air atmosphere.

The lower limit of the amount of the oxidizing agent used may be preferably 0.01 moles, more preferably 0.05 moles, and even more preferably 0.1 moles, relative to 1 mole of the organic compound that is a substrate. The upper limit of the amount of the oxidizing agent used is preferably 10 moles, more preferably 5.0 moles, and even more preferably 1.2 moles, relative to 1 mole of the organic compound that is a substrate. The amount of the oxidizing agent used is preferably in the range of 0.01 to 10 moles, more preferably in the range of 0.05 to 5.0 moles, and even more preferably 0.1 to 1.2 moles, relative to 1 mole of the organic compound that is a substrate. By carrying out the reaction with such an amount, the target product can be efficiently obtained.

The lower limit of the reaction temperature in step A is preferably −20° C., more preferably 0° C., and even more preferably 20° C.

The upper limit of the reaction temperature in step A is preferably 200° C., more preferably 150° C., and even more preferably 100° C.

The reaction temperature in step A is preferably in the range of −20 to 200° C., more preferably in the range of 0 to 150° C., and even more preferably in the range of 20 to 100° C.

By employing such a reaction temperature, the target product can be efficiently obtained.

The lower limit of the reaction time in step A is preferably 0.01 hour, more preferably 0.05 hour, and still more preferably 0.1 hour.

The upper limit of the reaction time in step A is preferably 72 hours, more preferably 48 hours, and even more preferably 24 hours.

The reaction time of step A is preferably within the range of 0.01 to 72 hours, more preferably within the range of 0.05 to 48 hours, and even more preferably within the range of 0.1 to 24 hours.

By employing such a reaction time, the target product can be efficiently obtained.

The reaction may be performed in the presence of inert gas (e.g., nitrogen gas), as long as the reaction of the present invention is not significantly impaired.

The carbonyl compound (1) obtained in step A may be purified by a known purification method, such as solvent extraction, desiccation, filtration, distillation, concentration, recrystallization, sublimation, column chromatography, and combinations thereof.

According to the production method of the present disclosure, the raw material conversion rate can be preferably 10% or more, more preferably 30% or more, and even more preferably 50% or more.

According to the production method of the present disclosure, the selectivity of the target compound can be preferably 80% or more, and more preferably 90% or more.

According to the production method of the present disclosure, the yield of the target compound is preferably 50% or more, and more preferably 70% or more.

EXAMPLES

Hereinafter, the present invention will be described in more detail with reference to Examples; however, the present invention is not limited thereto.

The meaning of the symbol and abbreviation in the Examples is shown below.

DMAc: dimethylacetamide

Example 1

10-Undecenol (9 g), DMAc (30 ml), and water (3 ml) were added to the container. PdCl$_2$ (0.5 mol %) and NaCl (0.17 eq.) were added thereto, and the inside of the container was placed in an oxygen atmosphere.

Thereafter, by heating at 80° C. for 15 hours, 11-hydroxyundecane-2-one, which was a target product, was obtained with a yield of 51%.

Example 2

The target product was obtained with a yield of 46% by the same method as in Example 1, except that KCl was added in place of NaCl.

Example 3

10-Undecenoic acid (4.7 g), DMF (30 ml), and water (3 ml) were added to the container. PdCl$_2$ (2.0 mol %) and NaCl (0.17 eq.) were added thereto, and the inside of the container was placed in an oxygen atmosphere.

Thereafter, by heating at 90° C. for 15 hours, 10-oxoundecanoic acid, which was a target product, was obtained with a yield of 60%.

Comparative Example 1

The target product was obtained with a yield of 23% by the same method as in Example 1, except that NaCl was not added.

The invention claimed is:

1. A method for producing a carbonyl compound represented by formula (1):

wherein
R¹ is hydrogen or an organic group;
R² is hydrogen or an organic group; and
R³ is hydrogen or an organic group; or
two or three of R¹, R², and R³ may be linked to form a ring that may have at least one substituent,
the method comprising step A of oxidizing an olefin compound represented by formula (2):

(2)

wherein R¹, R² and R³ are as defined above, by an oxidizing agent in the presence of
(a) a non-alcohol organic solvent, excluding an aromatic solvent and a nitrile solvent,
(b) water,
(c) a metal catalyst, and
(d) an additive represented by the formula: MXn
wherein
M is an element belonging to any one of Group 1, Group 2, Group 13, Group 14, and Group 15 in the periodic table, or $NR_4$, wherein R is hydrogen or a $C_{1-10}$ organic group;
X is halogen; and
n is a number of 1 to 5.

2. The production method according to claim 1, wherein R¹ and R² are independently hydrogen, $C_{1-10}$ alkyl optionally having at least one substituent, $C_{1-10}$ aromatic group optionally having at least one substituent, or a $C_{1-10}$ heterocyclic group optionally having at least one substituent.

3. The production method according to claim 2, wherein R¹ and R² are independently hydrogen; $C_{1-4}$ alkyl optionally having at least one substituent, wherein the at least one substituent is independently selected from the group consisting of hydroxyl, amino, carboxyl, sulfonic acid, phosphonic acid, and salts thereof; a $C_{1-10}$ aromatic group optionally having at least one substituent; or a $C_{1-10}$ heterocyclic group optionally having at least one substituent.

4. The production method according to claim 1, wherein R³ is hydrogen; $C_{1-20}$ alkyl optionally having at least one substituent; a $C_{1-20}$ aromatic group optionally having at least one substituent; or a $C_{1-20}$ heterocyclic group optionally having at least one substituent.

5. The production method according to claim 4, wherein R³ is hydrogen; $C_{1-20}$ alkyl optionally having at least one substituent, wherein the at least one substituent is independently selected from the group consisting of hydroxyl, amino, carboxyl, sulfonic acid, phosphonic acid, and salts thereof; a $C_{1-10}$ aromatic group optionally having at least one substituent; or a $C_{1-10}$ heterocyclic group optionally having at least one substituent.

6. The production method according to claim 1, wherein the non-alcohol organic solvent (a) is at least one solvent selected from the group consisting of an amide solvent, an ether solvent, a sulfoxide solvent, an ester solvent, a ketone solvent, a fluorine-based solvent, a carbonate solvent, a carboxylic acid solvent, and an ionic liquid.

7. The production method according to claim 6, wherein the non-alcohol organic solvent (a) is at least one solvent selected from the group consisting of an amide solvent, an ether solvent, and a carboxylic acid solvent.

8. The production method according to claim 7, wherein the non-alcohol organic solvent (a) is an amide solvent.

9. The production method according to claim 1, wherein the metal catalyst (c) is a transition metal catalyst.

10. The production method according to claim 9, wherein the metal catalyst (c) is at least one catalyst selected from the group consisting of a Ti catalyst, a Cr catalyst, a Fe catalyst, a Co catalyst, a Ni catalyst, a Mo catalyst, a Ru catalyst, a Rh catalyst, a Pd catalyst, a W catalyst, an Ir catalyst, a Pt catalyst, and an Au catalyst.

11. The production method according to claim 10, wherein the metal catalyst (c) is at least one catalyst selected from the group consisting of a Fe catalyst, a Ru catalyst, a Pd catalyst, and a W catalyst.

12. The production method according to claim 11, wherein the metal catalyst (c) is a Pd catalyst.

13. The production method according to claim 1, wherein the additive (d) is an additive represented by the formula: MXn
wherein
M is an element belonging to any one of Group 1, Group 2, Group 13, Group 14, and Group 15 in the periodic table, or $NR_4$, wherein R is hydrogen or a $C_{1-10}$ organic group;
X is halogen; and
n is a number of 1 to 3.

14. The production method according to claim 13, wherein the additive (d) is an additive represented by the formula: MXn
wherein
M is Li, B, Mg, Al, Si, P, K, Ca, Cs, or $NH_4$;
X is fluorine, chlorine, bromine, or iodine; and
n is a number of 1 to 3.

15. The production method according to claim 14, wherein the additive (d) is an additive represented by the formula: MXn
wherein
M is Li, Na, K, or $NH_4$;
X is chlorine; and
n is a number of 1.

16. The production method according to claim 1, wherein the oxidizing agent is at least one member selected from the group consisting of molecular oxygen, ozone, a quinone, a hypervalent iodine compound and a peroxyacid.

17. The production method according to claim 16, wherein the oxidizing agent is molecular oxygen.

* * * * *